United States Patent
Some (10) Patent No.: US 7,006,224 B2
(45) Date of Patent: Feb. 28, 2006

(54) METHOD AND SYSTEM FOR OPTICAL INSPECTION OF AN OBJECT

(75) Inventor: Daniel Some, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 257 days.

(21) Appl. No.: 10/453,149

(22) Filed: Jun. 2, 2003

(65) Prior Publication Data

US 2004/0125375 A1    Jul. 1, 2004

Related U.S. Application Data

(60) Provisional application No. 60/437,545, filed on Dec. 30, 2002.

(51) Int. Cl.
*G01J 4/00*    (2006.01)

(52) U.S. Cl. .................................................... 356/369
(58) Field of Classification Search .. 356/237.1–237.5, 356/364–370
See application file for complete search history.

(56) References Cited

U.S. PATENT DOCUMENTS

| | | | | |
|---|---|---|---|---|
| 4,893,932 A | * | 1/1990 | Knollenberg | 356/369 |
| 5,432,607 A | * | 7/1995 | Taubenblatt | 356/364 |
| 6,046,811 A | * | 4/2000 | Wolff et al. | 356/369 |
| 2003/0020904 A1 | * | 1/2003 | Uto et al. | 356/237.2 |
| 2003/0025905 A1 | * | 2/2003 | Meeks | 356/237.3 |

FOREIGN PATENT DOCUMENTS

| | | |
|---|---|---|
| WO | WO 02/25708 | 3/2002 |
| WO | WO 02/27288 | 4/2002 |
| WO | WO 02/40970 | 5/2002 |

OTHER PUBLICATIONS

"International Search Report", International Searching Authority, PCT/US 03/36837, (May 24, 2004).

* cited by examiner

*Primary Examiner*—Michael P. Stafira
(74) *Attorney, Agent, or Firm*—Tarek N. Fahmi (57) ABSTRACT

Systems and methods for optical inspection of patterned and non-patterned objects. The methods include determining a state of polarization of light reflected from the object, establishing a polarization state of the incident light, and filtering the reflected light by polarization so as to provide an optical signal that is detected by a detector.

44 Claims, 8 Drawing Sheets

FIGURE 4 determining a polarization shift introduced by the pattern and a polarization of an incident light beam that will be shifted by the pattern
210 establishing a polarization state of a light beam, in response to the determination, to provide an incident light beam that impinges on the patterned object
220 filtering a reflected light beam by polarization, in response to the determination, and generating a detection signal in response to a detection of the filtered reflected light beam
230

200     FIGURE 5

FIGURE 6 determining a polarization of an incident light beam that will be phase shifted by a defect
410 establishing a polarization state of a light beam, in response to the determination, to provide an incident light beam that impinges on the object
420

; filtering by polarization a reflected beam of light that is reflected from the unpatterned object so as to block the light reflected in the absence of a defect
430 generating a detection signal in response to a detection of the reflected light beam
440

METHOD AND SYSTEM FOR OPTICAL INSPECTION OF AN OBJECT

RELATED APPLICATIONS

This application claims the benefit of U.S. provisional application Ser. No. 60/437,545 filed Dec. 30, 2002, titled "optical configuration for detecting phase anomalies in birefringent substrates with normal illumination".

FIELD OF THE INVENTION

Optical inspection methods and systems and especially optical inspection for detecting sub-wavelength defects or process variations.

BACKGROUND OF THE INVENTION

A variety of systems are used for automated inspection of semiconductor wafers, in order to detect defects, particles and/or patterns on the wafer surface as part of a quality assurance process in semiconductor manufacturing processes. It is a goal of current inspection systems to detect defects.

The electric field component of light waves is used to define the state of polarization of said waves. Polarized light waves in general are said to be elliptically polarized—there may be a certain phase shift between two perpendicular electrical field components $E_x$ and $E_y$, $E_x$ and $E_y$ being the components of the electric field directed along the x and y directions, respectively, wherein the direction of propagation is in the z direction. The polarization state is often described by two parameters related to the ellipse generated by the electric field components: $\epsilon$ (the degree of ellipticity) and $\alpha$ (the orientation angle of the major axis). When the phase shift between the two electric field components is $k*\pi$ radians (k being an integer) the light wave is linearly polarized, $\epsilon=0$ and $\alpha=\arctan(\cos(k\pi)\cdot E_y/E_x)$. When both components have the same amplitude but are phase shifted in relation to each other by $(k+1/2)*\pi$ radians the light wave is said to be circularly polarized, and $\epsilon=1$ (in this case $\alpha$ is meaningless). For intermediate polarization states, $\epsilon$ is between 0 and 1 and $\alpha$ ranges between 0 and $\pi$.

The optical properties of anisotropic materials depend on the polarization as well as the direction of propagation of light waves. The propagation of electromagnetic waves through anisotropic materials is known in the art and is described in "Optical Waves in Crystals"; A. Yariv, P. Yeh, 1984 John Wiley & Sons, Inc. pages 69–120.

Birefringence is a property of an anisotropic material that has two different indices of refraction for light polarized in different directions (said directions known as the ordinary axis and extraordinary axis), to split a light wave into an ordinary component and to an extraordinary component, said components corresponding to the components of the incident electric field along the respective axes. Accordingly, a birefringent material may produce a phase shift between the two polarization components of a light wave and may also introduce a relative amplitude shift, thus it may change the state of polarization of a light wave. The phase shift between the ordinary component and the extraordinary component is termed phase retardation. Any change of either $\epsilon$ or $\alpha$ between the incident and reflected or transmitted light will be termed forthwith as a polarization shift.

A half wave plate is an optical element that produces a phase retardation of $\pi$ radians between the ordinary and extraordinary axes. Rotating a half wave plate such that one of said axes is set at an angle $\theta$ relative to the polarization direction of a linearly polarized light wave will, upon passage through the element, rotate the polarization direction of the light wave by $2\theta$, given that the incident beam is perpendicular to the plane of the half wave plate. Accordingly, a half wave plate that is rotated by $\pi/4$ radians relative to the incident polarization direction may convert a vertically polarized wave light to a horizontally polarized wave light.

A quarter wave plate is an optical element that produces a phase retardation of $\pi/2$ radians between the ordinary and extraordinary axes. Quarter wave plates that are oriented such that one of said axes creates an angle of $\pi/4$ radians relative to the polarization direction of a linearly polarized light wave will, upon passage through the element, convert the linearly polarized light into a circular polarized light; conversely, circularly polarized light which is perpendicularly incident on a quarter wave plate is converted to linearly polarized light with the polarization vector along an angle of $\pi/4$ radians relative to the ordinary axis.

A linear polarization filter is an optical element that transmits a particular linearly polarized component of an incident light beam, and blocks the component orthogonally polarized to said linear polarization of said light beam.

Any arbitrary elliptical polarization state of a light beam may be established through suitable application of a polarization filter, half wave plate and quarter wave plate: First the linear polarization filter is applied to the incident beam to establish a well-defined linear polarization, then the half wave plate and quarter wave plate are applied to the light beam in order to convert said linear polarization to the desired elliptical polarization. This process is termed forthwith as establishing the polarization state of the light beam.

Any arbitrary elliptical polarization component may be removed from a light beam through suitable application of a half wave plate, quarter wave plate and polarization filter. First the half wave plate and quarter wave plate are applied to the light beam in order to convert the desired elliptical polarization component into linear polarization, then the polarization filter is applied to the light beam to block said linear polarization. This process is termed forthwith as filtering the light beam by polarization.

U.S. Pat. No. 5,333,052 of Finarov describes a system and method that uses an obliquely illuminated, linearly polarized light beam to provide a contrast image, whereas the reflected light is filtered by polarization in response to the birefringence of a certain material of an inspected object. The system and method are used for detection of the presence of, or thickness variations in, transparent films.

SUMMARY OF THE INVENTION

The invention is based on the assumption that features and patterns present in a substrate may produce polarization shifts of the incident light, thus the state of polarization of the incident light differs from the state of polarization of reflected (or transmitted) light. In general this will occur in any pattern at the lateral boundaries between different materials and/or at the lateral boundaries of features having different heights. Notably, this usually occurs in repetitive patterns, and will occur uniformly in those repetitive patterns that are characterized by a pitch that is smaller than the wavelength of the incident light beam.

The inventors have found that by applying a null ellipsometric method the system and method for optical inspection can be highly sensitive and detect defects in the pattern smaller than the wavelength of the incident light, whereas the wavelength is smaller than 600 nanometer. In such a null ellipsometric method, the reflected (or transmitted) light is filtered by polarization so as to block optical signals from the non-defective pattern, whereas light traversing a defective pattern is subject to a different polarization shift and hence some portion of the optical signal will not be filtered and will reach the detector.

The invention provides a method for optical inspection of a patterned object, the method includes: determining a polarization shift introduced by the pattern and a polarization of an incident light beam that will be polarization shifted by the pattern; establishing a polarization state of a light beam, in response to the determination, to provide an incident light beam that impinges on the patterned object; filtering a reflected light beam by polarization, in response to the determination; and generating a detection signal in response to a detection of the filtered reflected light beam.

The invention provides a method for optical inspection of a patterned object, the method includes: determining a state of polarization of a reflected light beam that is reflected from the pattern; directing an incident light beam of light towards the patterned object; whereas the incident light beam is characterized by a state of polarization; filtering by polarization a reflected beam of light that is reflected from the patterned object in response to the determined state of polarization and directing the filtered reflected light towards a detector; and generating a detection signal in response to a detection of the filtered reflected light.

The invention provides a method for optical inspection of an unpatterned object, the method includes: determining a polarization of an incident light beam that will be polarization shifted by a defect; establishing a polarization state of a light beam, in response to the determination, to provide an incident light beam that impinges on the object; filtering by polarization a reflected beam of light that is reflected from the unpatterned object so as to block the light reflected in the absence of a defect; and generating a detection signal in response to a detection of the filtered reflected light beam.

The invention provides a system for optical inspection of an object, the system includes: incident light optics for establishing the polarization state of a light beam that is directed towards the object, such that the incident light beam shall be polarization shifted by the object; reflected light optics for filtering a reflected light beam by polarization, in response to an estimated polarization shift introduced by the object; and a detector, coupled to the controller, for generating a detection signal in response to a detection of the filtered reflected light beam.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

In the course of production of certain objects e.g. integrated circuits, certain patterns are produced. These patterns may have optical properties that differ from the optical properties of the materials from which the patterns are formed. Accordingly, a pattern may introduce a polarization shift between components of the electrical field of an incident light beam. Accordingly, the state of polarization of a reflected light beam differs from the state of polarization of the incident light beam.

Accordingly, a pattern may shift the state of polarization of an incident light beam in a different manner than the polarization shift introduced by any material that forms the pattern. When the pattern includes alternating materials (air or vacuum may also be considered materials for this purpose), where the repetition period is less than the wavelength of the incident light beam, the polarization shift will occur in a uniform manner over the entire pattern. When the pattern does not fulfill the aforementioned condition, it will produce polarization shifts that depend on position within the pattern.

A typical repetitive pattern includes multiple elongated conductors that are parallel to each other. The conductors are usually made of polycrystalline silicon, tungsten, aluminum or copper. In such a case the extraordinary axis of such a pattern is substantially parallel to that of the parallel conductors while the ordinary axis is substantially perpendicular to the parallel conductors. The retardation phase as well as the amplitude variation of the polarization components of light reflected from the pattern usually depends on various factors such as the repetition period, the width and height of the conductors, the refractive index of the conductors and the refractive index of the substrate.

The inventor has found that the polarization shift introduced by a defective pattern differs from the polarization shift of a non-defective pattern. A defective pattern may include particles, contaminants, breaks in the conductors, a short between the conductors, or the like. In cases where the polarization shift of light reflected from a non-defective pattern is zero, a defective pattern (such as a pattern that includes a oriented defect such as a scratch) can introduce a polarization shift that differs from zero.

Figure 1:
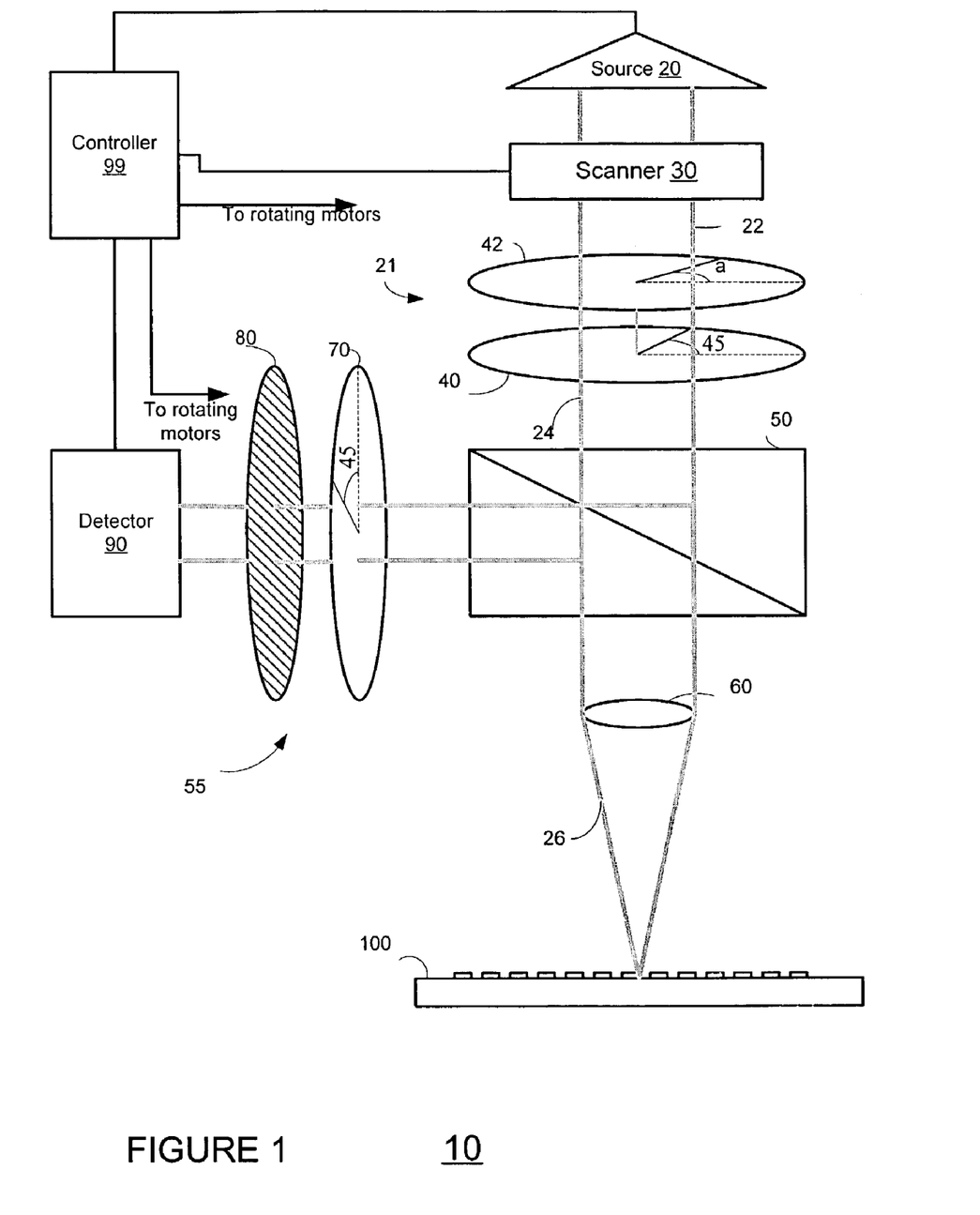
FIGS. 1–4 illustrate optical inspection systems, in accordance, with various embodiments of the invention.

According to an aspect of the invention the sensitivity of an optical system intended to detect defects in the pattern may be enhanced by implementing null ellipsometry principles. Accordingly, the polarization components of the reflected light are phase shifted relative to one another by polarization optical elements of the system in a manner that cancels (or largely suppresses) the phase shift that is introduced by a non-defective pattern, and a polarization filter is set to block the resultant polarized light, thus only a residual quantity of polarization shifted reflected light is detected. If the illuminated pattern is not defective only a small amount of light, if at all, is detected. Conversely, if the illuminated pattern is defective such that it shifts the polarization state differently than the non-defective pattern, the polarization filter will transmit a significant portion of the reflected light, causing a detected signal indicative of a defect. This method is especially appropriate under the condition that the pattern is repetitive on a pitch smaller than the wavelength of the incident light. However, in many instances it will be advantageous even when said condition is not fulfilled Referring now to FIG. 1, illustrating a system 10 for optical inspection of object 100. System 10 includes light source 20 and incident light optics 21. Light source 20 usually generates a light beam that has a preliminary state of polarization that may be changed prior to impinging on the object. Incident light optics 21 may include various polarizing components, such as quarter wave plates 40, and half wave plate 42. The incident light beam propagates along an optical axis and may propagate through additional components such as scanner 30, non-polarizing beam splitter 50, objective lens 60 and the like. It is assumed that a linearly polarized light beam 22 is scanned by scanner 30, for scanning beam 22 along a primary scan axis, though it is also possible to position the scanner 30 downstream from the polarization components 40 and 42. Scanner 30 may include an acousto-optic scanner, a rotating mirror, and the like. Usually, the object 100 is mechanically translated along a traverse scan axis.

Linearly polarized light beam 22 passes through quarter wave plates 40 that is oriented by $\pi/4$ radians relative to the polarization direction of a linearly polarized beam 22. Quarter wave plate 40 converts the linearly polarized light beam 22 into a circularly polarized light beam 24. It is noted that the $\pi/4$ radians orientation may require passing the beam through a half wave plate 42 disposed between the linearly polarized light source 20 and the quarter wave plate 40. Alternatively, if the incident light beam 22 is of some arbitrary elliptical polarization, half wave plate 42 and quarter wave plate 40 may be set correspondingly as is known to those skilled in the art so as to produce a circularly polarized beam 24. The circularly polarized light beam 24 is also referred to an incident light beam, and propagates through non-polarizing beam splitter 50, and objective lens 60, along a first optical axis 7 that is perpendicular to object 100. It is assumed that non-polarizing beam splitter 50 does not induce changes in the polarization of the transmitted beam; if in fact it is not ideal in this respect then the wave plates 40 and 42 may be appropriately set as known to those skilled in the art, so as to produce a circularly polarized beam upon passage through beam splitter 50. Objective lens 60 focuses the light beam 24 to a spot that has a diameter that is conveniently larger than the repetitive pitch of the repetitive pattern. Preferably, the diameter of the illuminating spot exceeds two or three repetitive pitches, in order to guarantee that the incident light is polarization shifted uniformly by the pattern.

Figure 8:
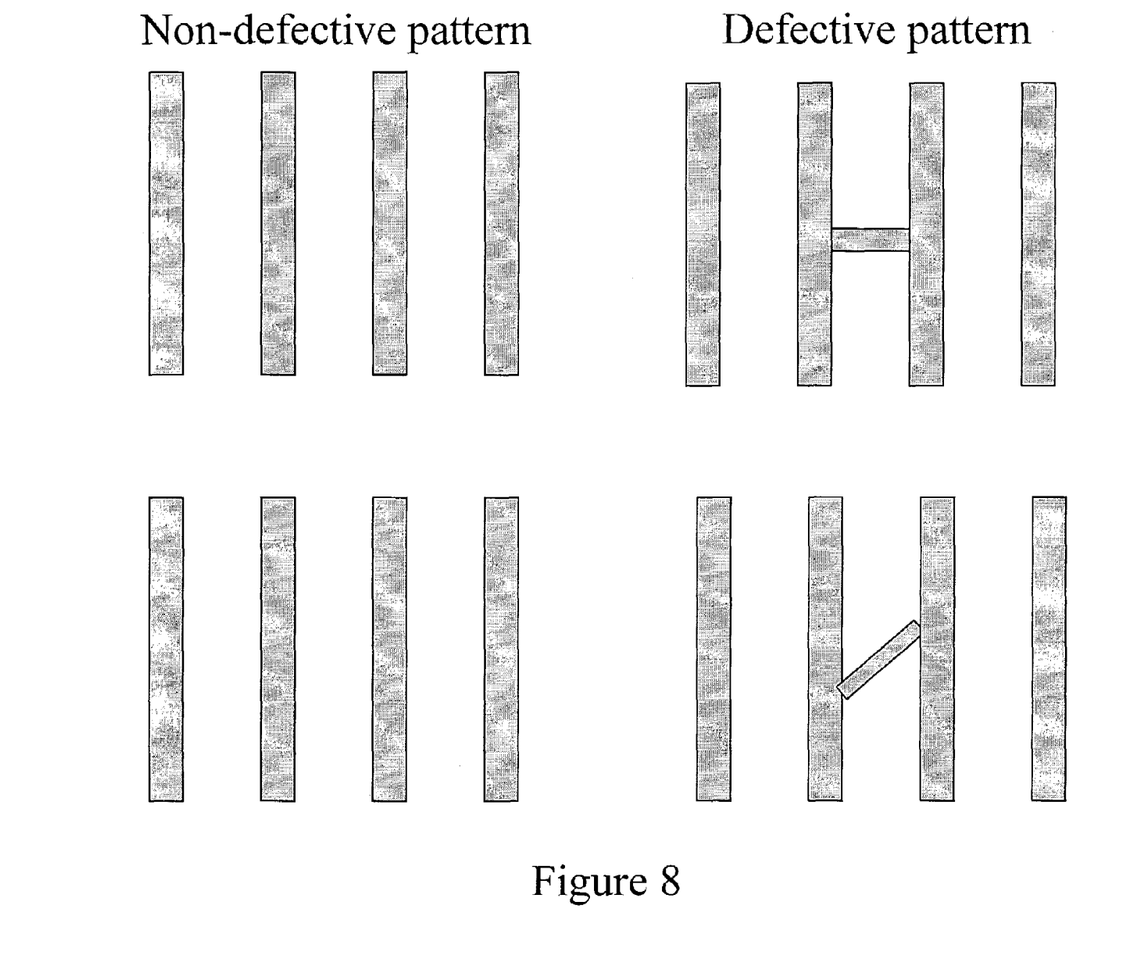
FIG. 8 illustrates an exemplary defective and non-defective portion of a pattern.

It is noted that the system and method do not necessarily require that the incident light beam be circularly polarized, though circular polarization is often optimal in that it is affected differently by the pattern and by most defects. In general the incident light beam should be polarized in such a manner as to induce a different polarization shift for defective and non-defective patterns, preferably maximizing said difference. If, for example, a non-defective pattern is characterized by an optical property affecting polarization relative to two distinct orientations (such as a first refractive index along an ordinary axis and another refractive index along an extraordinary axis) and the defective pattern retains these primary directions but changes the relative values of the property along each direction (such as illustrated at the upper part of FIG. 88), then the polarization of the incident light beam should not be oriented along one of the primary directions else it will not undergo a polarization shift for either the defective or non-defective pattern. The polarization of the incident light beam should be chosen such that it is subject to both of the primary directions; since the defective and non-defective patterns have different relative values of said optical property, then the resultant polarization will vary for the defective and non-defective pattern, producing different signals at the detector.

The lower part of FIG. 8 illustrates a defective pattern that does not retain the primary directions and therefore it is acceptable that the incident light be polarized along one of the primary directions of the non-defective pattern; the non-defective pattern will not shift the polarization of the reflected light while the defective pattern will do so.

In other words, when inspecting patterned objects that are expected to introduce a polarization shift, the incident light must be polarized in response to the orientations inducing polarization shifts by the defective or non-defective pattern. Accordingly, if the non-defective pattern has an ordinary axis and an extraordinary axis the incident light shall preferably have an ordinary component as well as an extraordinary component. For example, if the ordinary axis of the pattern is vertical and the extraordinary axis of the pattern is horizontal, the incident light should have both vertical and horizontal electrical field components. Such a pattern shall not be illuminated by a vertically polarized incident light beam or by a horizontally polarized incident light beam, but other elliptically polarized light beams can be utilized (including linearly polarized beams having a polarization direction that is oriented with respect to the vertical and horizontal axis).

A reflected light beam, such as polarization shifted reflected light beam 26 vertically propagates towards non-polarizing beam splitter 50, via reflective light optics 55 to be detected by detector 90. The reflected light optics 55 may include phase compensators and polarizer filters that are rotated about an optical axis 9 defined by the non-polarizing beam splitter 50 and detector 90, in a manner that extinguishes light reflected from non-defective patterns. The phase compensator is usually a quarter wave plate, such as quarter wave plate 70, and the polarizer filters include an analyzer 80. The phase compensator may also be a liquid crystal variable retarder. Analyzer 80 includes a polarizing filter that is rotated about the optical axis of the reflected light by a motor (not shown).

Reflected light optics 55 may be configured (by rotation of some of its components) during a preliminary step that involves providing a non-defective pattern, illuminating the pattern and rotating the second polarization optic components until a minimal signal reaches the detector. Minimizing the signal may be accomplished through trial-and-error, or may be accomplished by measuring the polarization state of the reflected light incident on the polarization filter 80 and rotating the wave plate 70 and polarization filter 80 in a known manner so as to extinguish the signal upon passage through filter 80. The measurement may be accomplished in the following manner: 1) Measure the values $I_0$, $I_{90}$ and $I_{45}$ of the detected signal for three positions of polarizer 80: 0°, 90° and 45°, respectively. 2) If any of these values equals zero then the light is linearly polarized perpendicular to that direction; else, 3) Calculate the normalized values $E_x$ and $E_y$ of the electric field as $I_x/(I_x+I_y)$ and $I_y/(I_x+I_y)$, respectively. 4) Calculate the phase shift $\theta$ between the electric field components as $\cos(\theta)=[I_{45}-(I_0+I_{90})/2]/(I_0 I_{90})$. Once these values are calculated, the quarter wave plate 70 may be rotated appropriately so as to produce a linear polarization ($\theta=0°$) and the polarizer 80 may be rotated to extinguish light of the resultant linear polarization. The configuration may also be based upon a calculation of the phase shift introduced by a non-defective pattern and the state of polarization of the incident light, by modeling the sample structure and simulating electromagnetic propagation for light incident upon that structure using, e.g., finite element methods or rigorous coupled-wave analysis. According to yet another aspect of the invention a set of predefined configurations are provided and evaluated in order to select the best configuration.

Ideally the second polarization optics, or at least one of its components is located in a plane in which the scanned beam is stationary. Such a plane may be located at the exit pupil of the objective lens.

Defects are detected upon scanning an area of the patterned object and comparing detection signals from detector 90 with a nominal reference signal, e.g. the signal generated upon scanning a nominally identical adjacent region (die-to-die), or with the signal in the surrounding area, as per any of the standard inspection algorithms.

Detector 90 as well as motors for rotating various optical components, such as analyzer 80, are connected to and controlled by a controller 99, that is further capable of processing detection defects and determine the presence of a defect or of a process variation.

According to another aspect of the invention the detection signals may also be used for process variations monitoring. The polarization shift introduced by a non-defective pattern is responsive to geometry of the repetitive pattern. Accordingly, changes in the orientation of the conductors, width of the conductors or the repetitive period may alter the polarization shift introduced by the pattern. By processing detected signals from areas that well exceed the light beam diameter size process variations may be detected.

The system may also be operated for optical inspection of unpatterned areas of the object. The unpatterned areas are not supposed to introduce a polarization shift, whereas some defects may introduce a polarization shift. Accordingly, the reflected light optics is configured to filter by polarization reflected light from non-defective unpatterned areas.

The inventors have found that applying the invention for monitoring non-patterned areas of an object that include a transparent overlayer (or at least a partially transparent overlayer) may provide a robust inspection method that is not sensitive to changes in the thickness of the overlay layer. In other words the invention is not sensitive to color variations.

Figure 2:
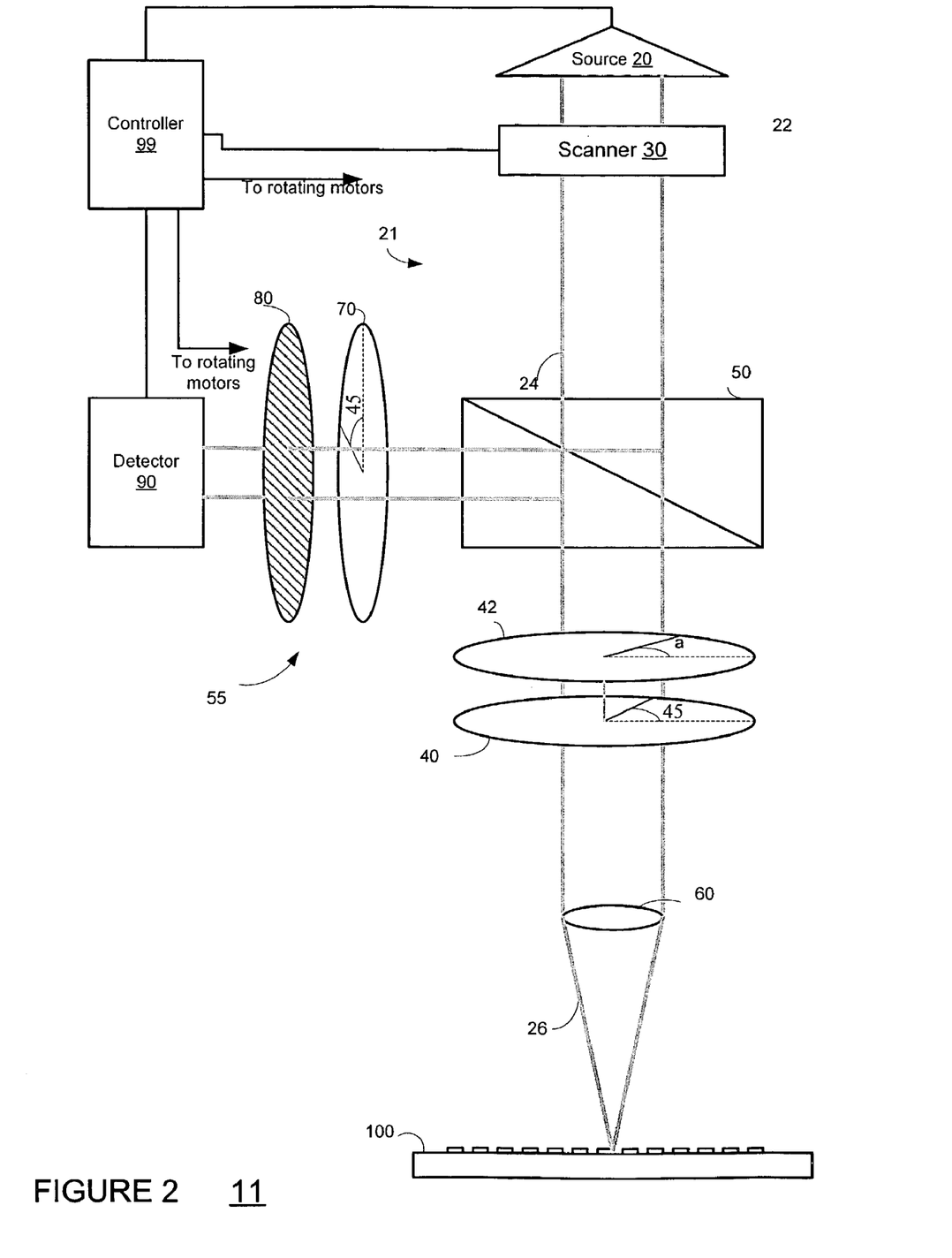

FIG. 2 illustrates system 11 that resembles system 10 but differs from said system as quarter wave plates 40 and half wave plate 42 are positioned between non-polarizing beam splitter 50 and objective lens 60, instead of being positioned between the linearly polarized light source 20 and non-polarizing beam splitter 50. In system 11 the quarter wave plate 40 and the half wave plate 42 are part of the incident light optics as well as the reflected light optics.

When using normal incidence the system facilitates optical inspection of unpatterned and patterned objects (including periodically patterned objects) with reduced susceptibility to color variation effects.

It is noted that if (a) a circularly polarized light is incident on a substrate and, (b) the substrate does not induce a polarization shift, then the light beam that exits the quarter wave plate (after being reflected from the surface) is linearly polarized with polarization vector perpendicular to that of the light incident on the quarter wave plate. It is further noted that if (a) a linearly polarized light is incident on a substrate, and (b) the substrate does not induce a polarization shift, then the reflected light beam is linearly polarized with polarization vector parallel to that of the light incident on the half wave plate (irrespective of the orientation of the incident polarization angle).

Accordingly, these characteristics of system 11 may simplify the procedure for setting the polarization components 70 and 80 and may in fact render some of them superfluous.

For example, if the incident light beam is linearly polarized incident light on a substrate that does not induce a polarization shift then polarization components 70 and 80 and non-polarizing beamsplitter 50 may be replaced by a polarizing beamsplitter which fulfills the function of polarizer 80 at a fixed angle. The portion of the illumination beam lost upon first passage through the beamsplitter 50 will then be regained through use of a polarizing beamsplitter in place of non-polarizing beamsplitter 50, if the incident beam 24 is of the proper linear polarization, as is know to those skilled in the art.

According to another embodiment of the invention the system can be used to detect defects in unpatterned objects. Such a system may include a polarizing beam-splitter (instead of the non-polarizing beam splitter 50) and an optional half wave plate positioned between polarizing beam-splitter and an objective lens.

According to another embodiment of the invention the system may include the non-polarizing beam splitter 50, a half wave plate or a quarter wave plate positioned between the objective lens and non-polarizing beam splitter 50 and a fixed polarizer that is positioned at an optical path between non-polarizing beam splitter and a detector.

Figure 3:
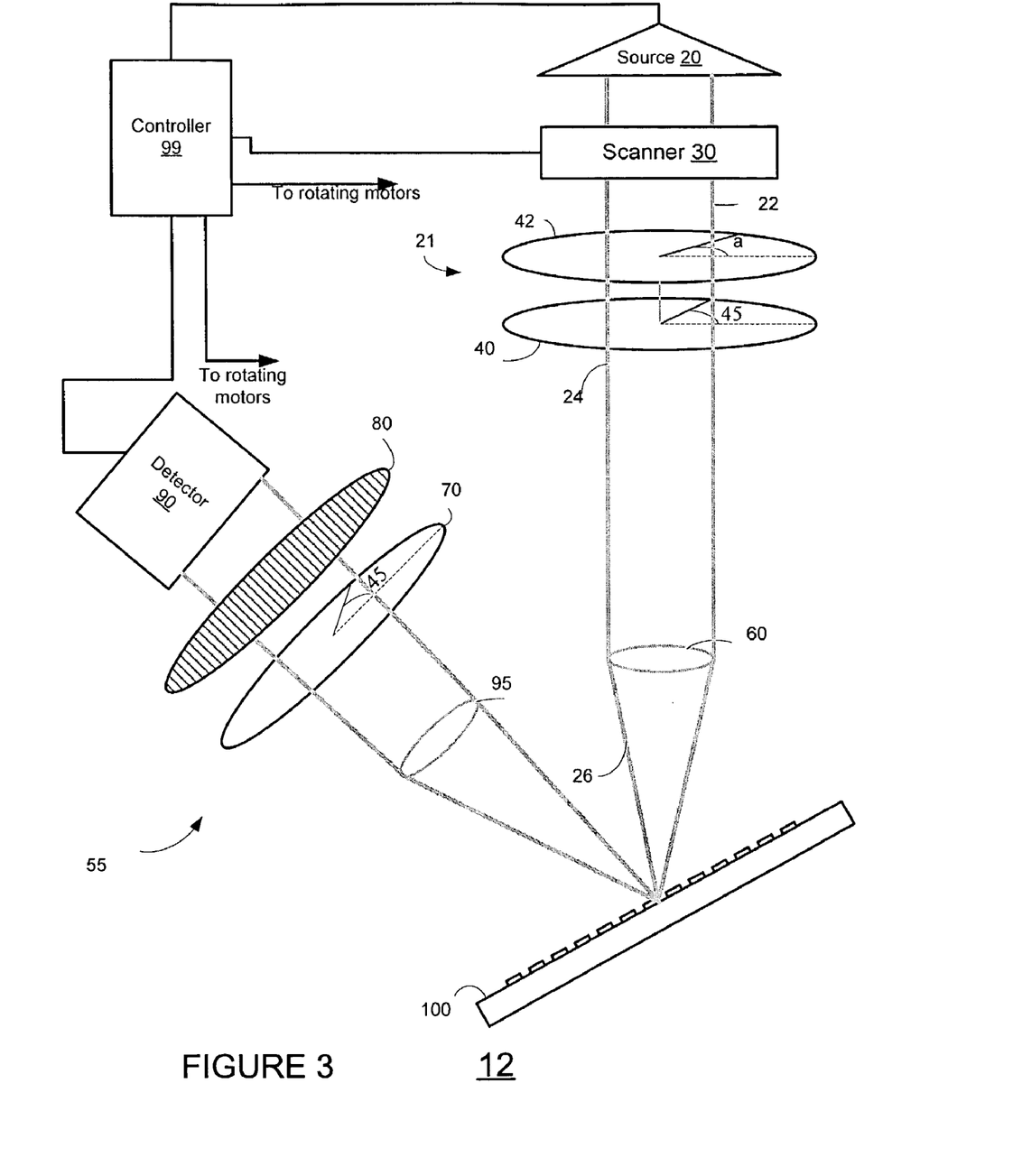

FIG. 3 illustrates a system 12 that resembles system 10 but implements oblique-illumination laser scanning instead of normal illumination laser scanning optics. Accordingly non-polarizing beam splitter 50 is removed, and another objective lens 95 is positioned such as to collect the specularly reflected beam from the object. The reflected light optics is positioned between the other objective lens 95 and detector 90.

Figure 4:
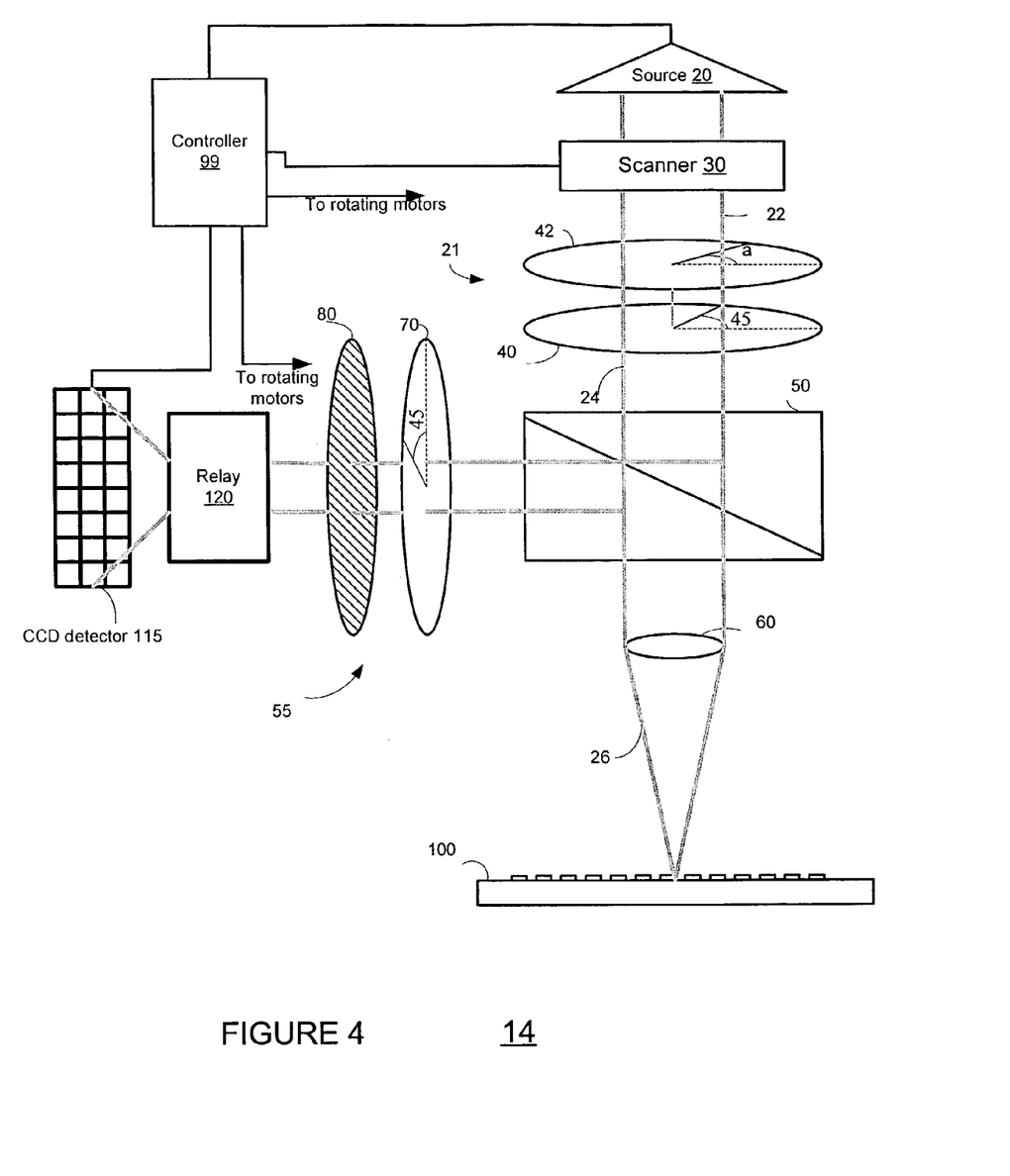

FIG. 4 illustrates system 14 that resembles system 10 but includes imaging optics 110. Imaging optics 110 includes imaging detector, such as CCD area array detector 115 and relay 120 positioned such as to image the inspected object onto CCD array detector 115. System 14 includes a light source that illuminates an area of the object corresponding to an at least portion of the area imaged onto the imaging detector. The pixel size or more especially the image resolution should preferentially correspond to several repetitive periods of the repetitive pattern. Scanning may be accomplished by translating or rotating the wafer, deflecting the illumination beam, or a combination thereof.

Figure 5:
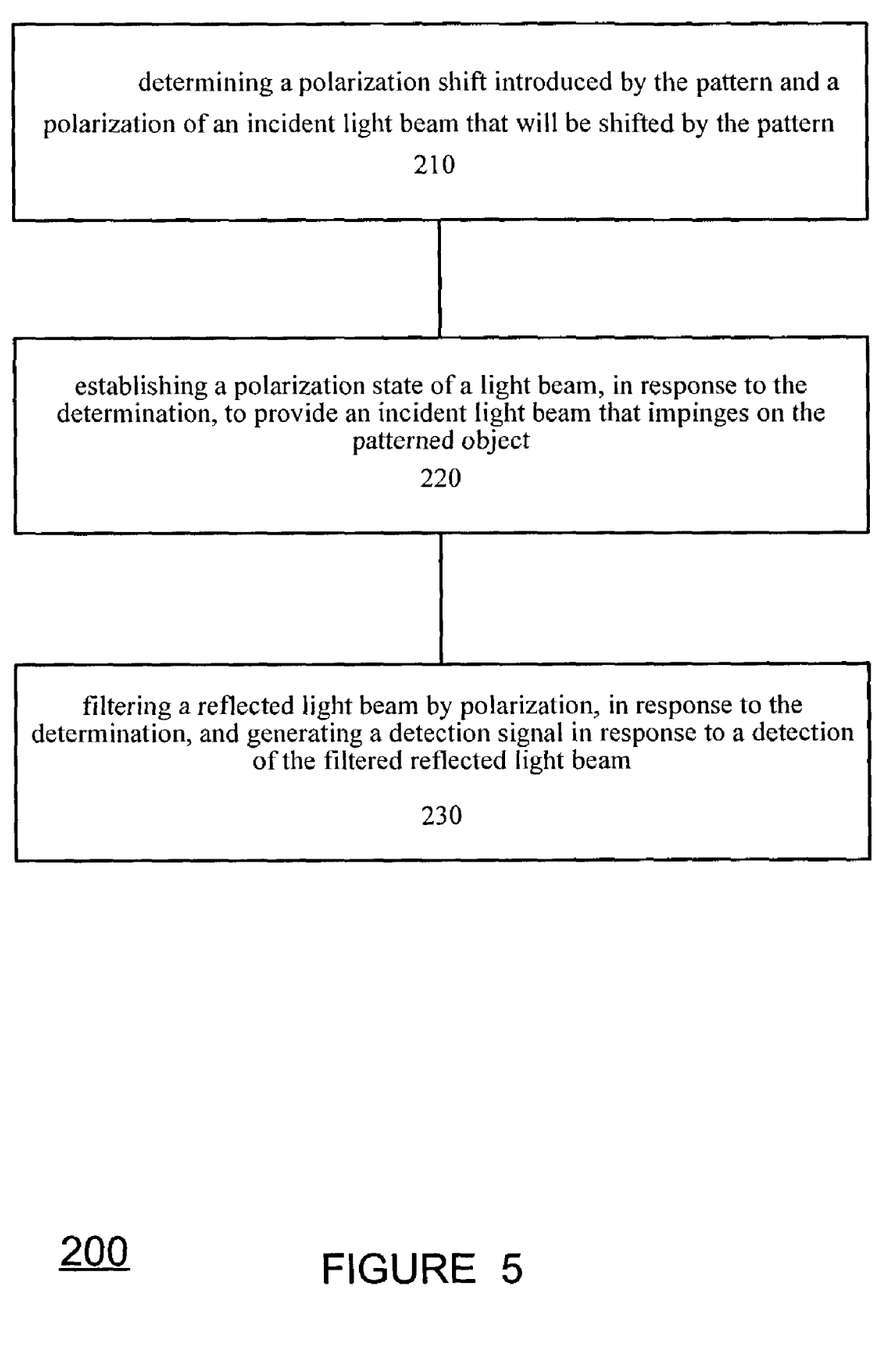
FIGS. 5–7 are flow chart diagrams of methods for optical inspection in accordance with various embodiments of the invention.

FIG. 5 illustrates method 200 for optical inspection. Method 200 includes the steps of: determining a polarization shift introduced by the pattern and a polarization of an incident light beam that will be shifted by the pattern (step 210), establishing a polarization state of a light beam, in response to the determination, to provide an incident light beam that impinges on the patterned object (step 220), filtering a reflected light beam by polarization, in response to the determination, and generating a detection signal in response to a detection of the filtered reflected light beam (step 230).

Figure 6:
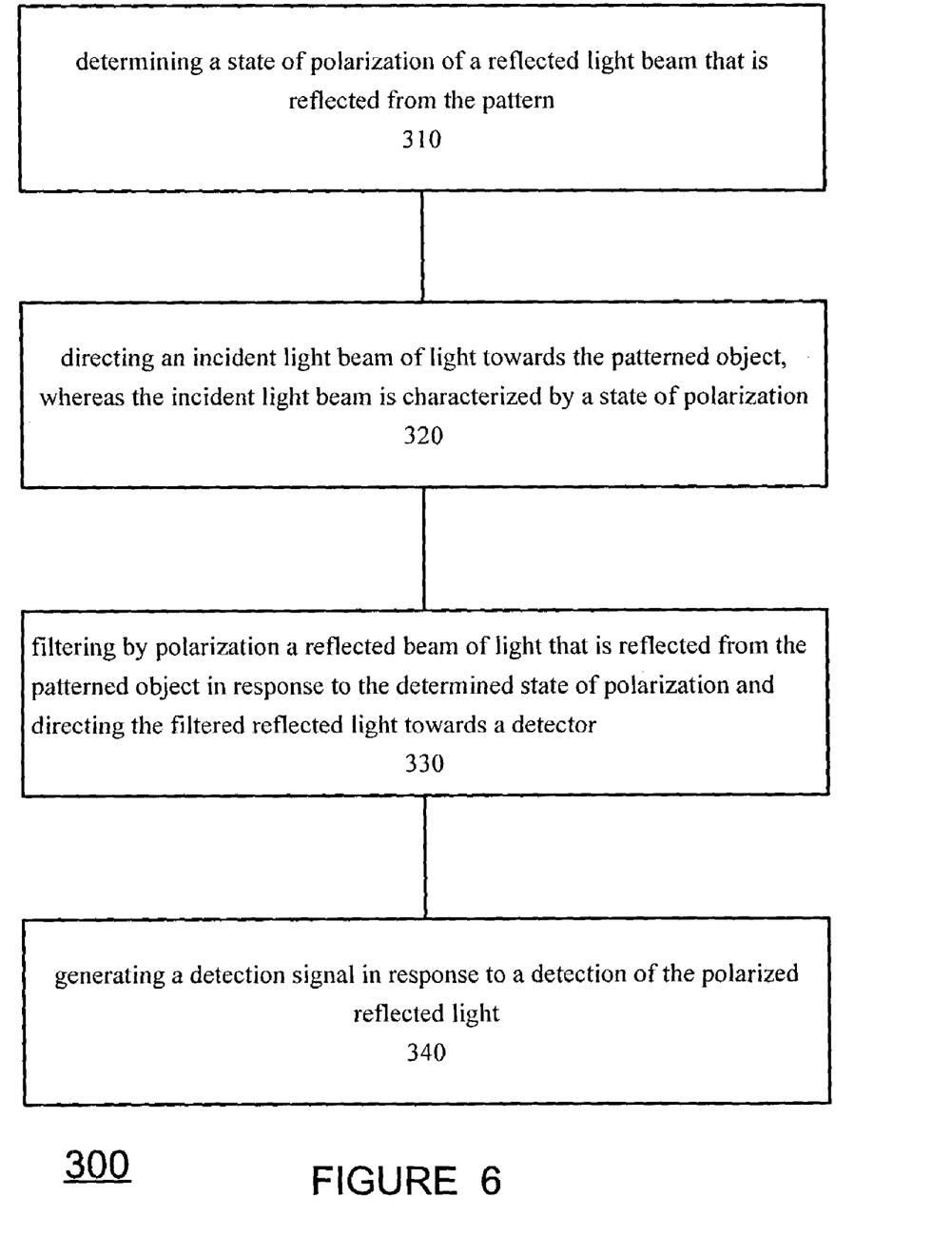

FIG. 6 illustrates method 300 for optical inspection. Method 300 includes the steps of: determining a state of polarization of a reflected light beam that is reflected from the pattern (step 310), directing an incident beam of light towards the patterned object, whereas the incident light beam is characterized by a state of polarization (step 320), filtering by polarization a reflected beam of light that is reflected from the patterned object in response to the determined state of polarization and directing the filtered reflected light towards a detector (step 330), and generating a detection signal in response to a detection of the filtered reflected light (step 340).

Figure 7:
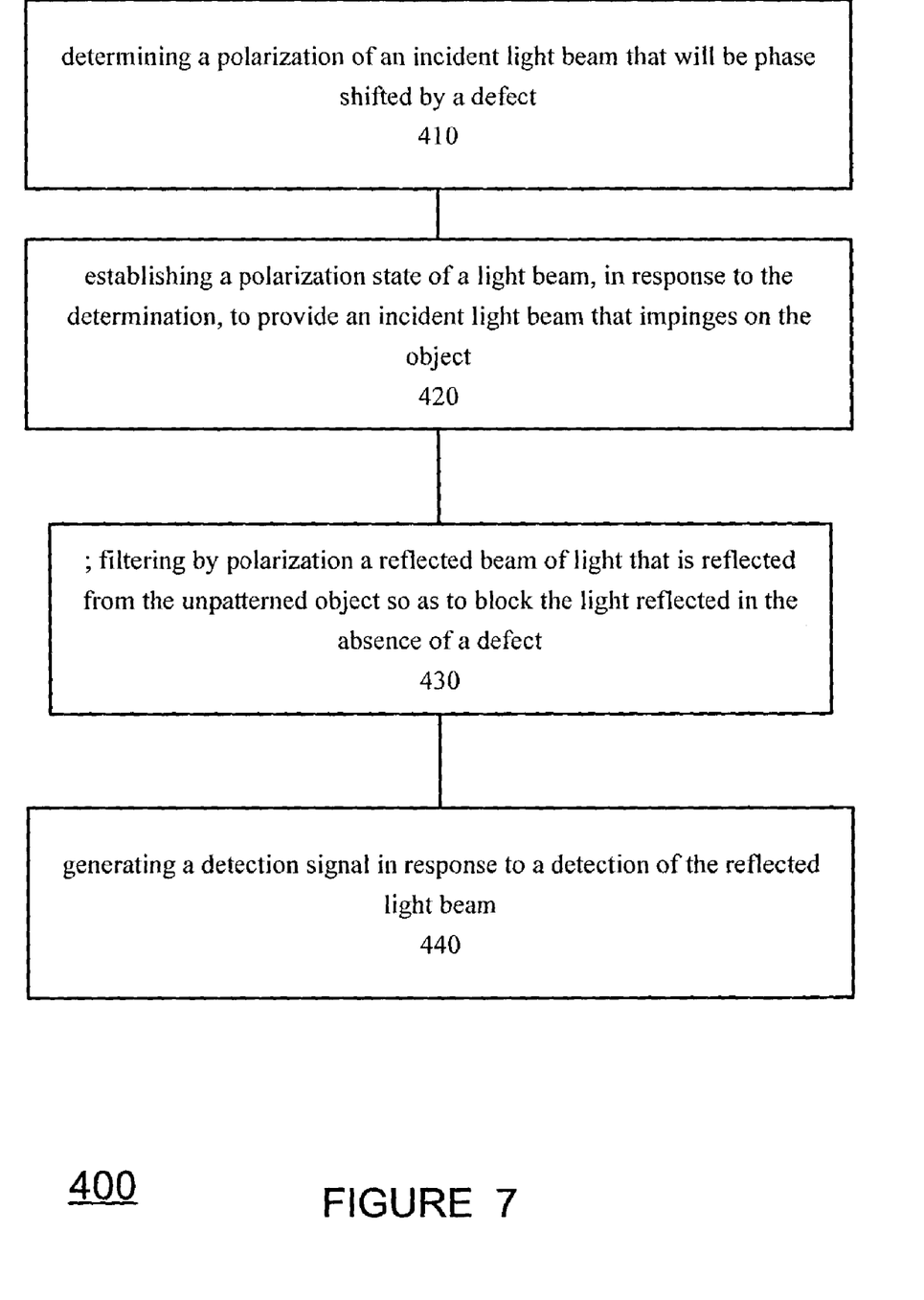

FIG. 7 illustrates method 400 for optical inspection of an unpatterned object. Method 400 includes the steps of: determining a polarization of an incident light beam that will be polarization shifted by a defect (step 410), establishing a polarization state of a light beam, in response to the determination, to provide an incident light beam that impinges on the object (step 420); filtering by polarization a reflected beam of light that is reflected from the unpatterned object so as to block the light reflected in the absence of a defect (step 430); and generating a detection signal in response to a detection of the reflected light beam (step 440). Step 410 may include estimating probable defects in response to previously detected defects, or in response to some characteristics of the manufacturing process of the object. In many cases a circular polarization may be selected, or a linear polarization having its polarization direction oriented with respect to the direction of probable defects.

Although certain polarizing components are described hereinabove with reference to particular systems 10, 11 and 14, the principles of the present invention may be applied to other types of inspection systems, using such alternative polarizing schemes as will be apparent to those skilled in the art. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

I claim:

1. A method for optical inspection of a patterned object, the method comprising the steps of:
    determining a polarization shift introduced by a pattern on the patterned object and a polarization of an incident light beam that will be polarization shifted by the pattern;
    establishing a polarization state of a light beam, in response to the determination, to provide a polarized incident light beam that impinges on the patterned object as a spot having a diameter larger than a repetitive pitch of the pattern;
    filtering a reflected light beam by polarization, in response to the determination; and
    generating a detection signal in response to a detection of the filtered reflected light beam.

2. The method of claim 1 wherein the step of determining comprises determining an ordinary axis and an extraordinary axis of the pattern.

3. The method of claim 2 wherein the step of determining comprises defining a polarization of the incident light beam to include an extraordinary component and an ordinary component.

4. The method of claim 1 wherein the reflected light beam is filtered by polarization such as to substantially reduce light components reflected from a non-defective pattern.

5. The method of claim 1 wherein the step of establishing a polarization state of a light beam comprises generating a circularly polarized incident light beam.

6. The method of claim 1 wherein the step of determining comprises a preliminary step of calculating the polarization shift.

7. The method of claim 1 wherein the step of determining comprises a preliminary step of measuring the polarization shift.

8. The method of claim 1 wherein the incident light beam propagates along an optical axis that is perpendicular to the patterned object.

9. The method of claim 1 wherein the incident light beam propagates along an optical axis that is oriented obliquely in relation to the patterned object.

10. The method of claim 1 further comprising a step of processing multiple detection signals to indicate a presence of a process variation.

11. The method of claim 1 further comprising a step of processing at least one detection signal to indicate a presence of a defect.

12. A method for optical inspection of a patterned object, the method comprising the steps of:
    determining a state of polarization of a reflected light beam that is reflected from a pattern on the patterned object;
    directing an incident beam of light towards the patterned object so as to impinge on the patterned object as a spot having a diameter larger than a repetitive pitch of the pattern; whereas the incident light beam is characterized by a state of polarization; filtering by polarization a reflected beam of light that is reflected from the patterned object in response to the determined state of polarization and directing the filtered reflected light towards a detector; and
    generating a detection signal in response to a detection of the filtered reflected light.

13. The method of claim 12 further comprising a step of processing at least one detection signal to indicate a presence of a defect.

14. The method of claim 12 further comprising a step of processing multiple detection signals associated with at least one area of the patterned object to indicate a presence of a process variation.

15. The method of claim 12 further comprising a step of generating an image of the patterned object out of at least one detection signal.

16. The method of claim 12 wherein the step of filtering by polarization comprises filtering such as to substantially reduce light reflected from a non-defective pattern.

17. The method of claim 12 wherein the step of determining comprises a preliminary step of calculating the state of polarization of the light that is reflected from the pattern.

18. The method of claim 12 wherein the step of determining comprises a preliminary step of measuring the state of polarization of the light that is reflected from the pattern.

19. A method for optical inspection of an unpatterned object, the method comprising the steps of:
    determining a polarization of an incident light beam that will be polarization shifted by a defect;
    establishing a polarization state of a light beam, in response to the determination, to provide an incident light beam that impinges on the object;
    filtering by polarization a reflected beam of light that is reflected from the unpatterned object so as to block the light reflected in the absence of a defect; and
    generating a detection signal in response to a detection of the reflected light beam.

20. The method of claim 19 further comprising a step of filtering the reflected light beam by polarization.

21. The method of claim 20 wherein the reflected light beam is filtered by polarization such as to substantially reduce light components reflected from a non-defective object.

22. The method of claim 19 wherein the step of establishing the polarization state of a light beam comprises generating a circularly polarized incident light beam.

23. The method of claim 19 wherein the incident light beam propagates along an optical axis that is perpendicular to the patterned object.

24. The method of claim 19 further comprising a step of processing multiple detection signals to indicate a presence of a process variation.

25. The method of claim 19 further comprising a step of processing at least one detection signal to indicate a presence of a defect.

26. The method of claim 1 wherein the detection signal represents an image of an area of the patterned object.

27. The method of claim 19 wherein the detection signal represents an image of an area of the patterned object.

28. A system for optical inspection of an object, the system comprising:
   incident light optics for establishing the polarization state of a light beam that is directed towards the object so as to impinge thereon as a spot having a diameter greater than a pitch of a pattern on the object, such that the incident light beam shall be polarization shifted by the object;
   reflected light optics for filtering a reflected light beam by polarization, in response to an estimated polarization shift introduced by the object; and
   a detector, coupled to the controller, for generating a detection signal in response to a detection of the filtered reflected light beam.

29. The system of claim 28 wherein the detector is an imaging detector and the reflected light optics are capable of providing an image of an area of the object on the detector.

30. The system of claim 28 wherein the detector is a non-imaging detector and the reflected light optics produce a pupil at the detector.

31. The system of claim 28 wherein the incident light optics direct the incident light beam along an optical axis that is perpendicular to the object.

32. The system of claim 28 wherein the incident light optics direct the incident light beam along an optical axis that is oriented obliquely in relation to the object.

33. The system of claim 28 wherein the incident light optics are capable of establishing a linear state of polarization along any orientation within a plane of the object.

34. The system of claim 28 wherein the incident light optics are capable of establishing a circular state of polarization within a plane of the object.

35. The system of claim 28 wherein the incident light optics are capable of establishing any elliptical state of polarization within a plane of the object.

36. The system of claim 28 wherein the reflected light optics are capable of filtering the reflected light beam by polarization such as to substantially reduce light components reflected from a non-defective pattern.

37. The system of claim 28 wherein retarders responsible for establishing the polarization state of the light beam that is directed towards the object are also present in the path of the reflected light beam.

38. The system of claim 28 wherein retarders responsible for establishing the polarization state of the light beam that is directed towards the object are separate from those used to filter by polarization the reflected light beam.

39. The system of claim 28 further comprising a polarizing beamsplitter configured for a) transmitting the light beam towards the object and reflecting the reflected light beam towards the detector, as well as b) filtering by polarization the reflected light beam.

40. The system of claim 28 further comprising a non-polarizing beamsplitter configured for transmitting the light beam towards the object and reflecting the reflected light beam towards the detector, and an independent polarization filter configured to filter by polarization the reflected light beam.

41. The system of claim 28 wherein the system is capable of calculating the polarization shift.

42. The system of claim 28 wherein the system is capable of measuring the polarization shift.

43. The system of claim 28 further comprising a processor, coupled to the detector, that is capable of processing multiple detection signals to indicate a presence of a process variation.

44. The system of claim 28 further comprising a processor, coupled to the detector, that is capable of processing at least one detection signal to indicate a presence of a defect.

* * * * *